United States Patent
Ebata (10) Patent No.: US 12,343,214 B2
(45) Date of Patent: Jul. 1, 2025

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Tetsurou Ebata, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 143 days.

(21) Appl. No.: 18/176,157

(22) Filed: Feb. 28, 2023

(65) Prior Publication Data
US 2023/0301636 A1    Sep. 28, 2023

(30) Foreign Application Priority Data

Mar. 23, 2022   (JP) .................. 2022-047001

(51) Int. Cl.
*A61B 8/00*   (2006.01)
*A61B 8/08*   (2006.01)

(52) U.S. Cl.
CPC .............. *A61B 8/54* (2013.01); *A61B 8/0825* (2013.01); *A61B 8/42* (2013.01)

(58) Field of Classification Search
CPC ........... A61B 8/54; A61B 8/0825; A61B 8/42; A61B 8/4281; A61B 8/5207; A61B 8/5223
See application file for complete search history.

(56) References Cited

U.S. PATENT DOCUMENTS

| | | | |
|---|---|---|---|
| 2020/0188538 A1* | 6/2020 | Scurtescu | A61P 1/02 |
| 2021/0373154 A1* | 12/2021 | Wang | A61B 8/58 |
| 2024/0008839 A1* | 1/2024 | Yoo | A61B 5/015 |
| 2024/0193764 A1* | 6/2024 | Speter | A61B 8/488 |

FOREIGN PATENT DOCUMENTS

| | | | |
|---|---|---|---|
| JP | 2004-049558 A | | 2/2004 |
| JP | 2018-175007 A | | 11/2018 |
| WO | WO 2018036912 | * | 3/2018 |
| WO | WO2018070760 | * | 4/2018 |

* cited by examiner

*Primary Examiner* — Alexei Bykhovski
(74) *Attorney, Agent, or Firm* — Studebaker Brackett PLLC (57) ABSTRACT

There are provided an ultrasound diagnostic apparatus and a control method of the ultrasound diagnostic apparatus which can accurately specify an examination position of a subject by an examiner while ensuring a subject's privacy. The ultrasound diagnostic apparatus for the examiner to perform ultrasonography on symmetrically disposed measurement sites of the subject by using an ultrasound probe includes a gel region detection unit that detects a temporal change of a gel region where gel is applied to the examination position of the subject; and an examination position estimation unit that estimates the examination position of the subject on the basis of a position where the temporal change of the gel region is detected by the gel region detection unit.

15 Claims, 5 Drawing Sheets

ULTRASOUND DIAGNOSTIC APPARATUS AND CONTROL METHOD OF ULTRASOUND DIAGNOSTIC APPARATUS

CROSS-REFERENCE TO RELATED APPLICATIONS

The present application claims priority under 35 U.S.C. § 119 to Japanese Patent Application No. 2022-047001, filed on Mar. 23, 2022. The above application is hereby expressly incorporated by reference, in its entirety, into the present application.

BACKGROUND OF THE INVENTION

1. Field of the Invention

The present invention relates to an ultrasound diagnostic apparatus, and a control method of the ultrasound diagnostic apparatus which examine symmetrical sites of a subject.

2. Description of the Related Art

In the related art, ultrasonography is performed on a subject by capturing an ultrasound image using a so-called ultrasound diagnostic apparatus. In particular, in a case where sites of the subject that are disposed at generally symmetrical positions, such as the breast, kidneys, and lungs of the subject are examined, in order to easily determine which of the left and right sites of the subject is imaged in the captured ultrasound image, a so-called body mark indicating an examination position is often set on the ultrasound image. Such a body mark is often set manually by an examiner.

Since it is usually difficult to determine which of the left and right sites of the subject is imaged in the ultrasound image by checking the ultrasound image, in a case where an incorrect body mark is set, it is difficult to check the ultrasound image after the examination and correctly set the body mark. Thus, for example, as disclosed in JP2018-175007A and JP2004-049558A, a technique of automatically specifying an examination site of a subject is disclosed. JP2018-175007A discloses that the examination site of the subject is specified by performing image processing on an image of the subject captured by an optical camera or the like and detecting the position and orientation of the ultrasound probe. JP2004-049558A discloses that, in a case where a so-called High Intensity Focused Ultrasound (HIFU) treatment, which causes necrosis of a lesion part by emitting ultrasonic waves to focus thermal energy on the lesion part, is performed, the temperature at a location heated by the ultrasonic waves is monitored to detect a treatment position.

SUMMARY OF THE INVENTION

However, since the orientation of the ultrasound probe is variously changed depending on the holding way by the examiner, even in a case where an attempt is made to detect the ultrasound probe by the image processing as disclosed in JP2018-175007A, the detection fails and the examination position cannot be specified accurately in some cases. Further, in a case where an optical image of the subject is captured, for example, there is also a problem that the optical image in which the subject's face or the like is shown is acquired so that the subject's privacy cannot be ensured. The technique of JP2004-049558A has a problem that the technique cannot be applied to normal ultrasonography in which the HIFU treatment is not performed.

The present invention is made to resolve such a problem in the related art, and an object thereof is to provide an ultrasound diagnostic apparatus and a control method of the ultrasound diagnostic apparatus which can accurately specify the examination position of the subject by the examiner while ensuring the subject's privacy.

In order to achieve the object, an ultrasound diagnostic apparatus according to an aspect of the present invention is an ultrasound diagnostic apparatus for an examiner to perform ultrasonography on symmetrically disposed measurement sites of a subject by using an ultrasound probe, and the ultrasound diagnostic apparatus includes a gel region detection unit that detects a temporal change of a gel region where gel is applied to an examination position of the subject; and an examination position estimation unit that estimates the examination position of the subject on the basis of a position where the temporal change of the gel region is detected by the gel region detection unit.

The measurement sites can be any one of breasts, kidneys, or lungs.

Further, in a case where the gel having a temperature different from a body surface temperature of the subject is applied to the examination position of the subject, the gel region detection unit can include a temperature sensor that acquires a temperature distribution of a body surface of the subject, and a temporal change detection unit that detects the temporal change of the gel region where the gel is applied to the subject by analyzing the temperature distribution acquired by the temperature sensor.

The temporal change detection unit can detect the temporal change of the gel region by excluding the ultrasound probe and a hand of the examiner from the temperature distribution acquired by the temperature sensor.

The ultrasound diagnostic apparatus can further include a notification unit that performs a notification to the examiner.

The gel having a temperature higher than the body surface temperature of the subject can be applied to the examination position of the subject, and the notification unit can issue a warning in a case where a temperature of the gel region acquired by the temperature sensor is lowered to be equal to or lower than a predetermined first temperature.

Further, the notification unit can issue a warning in a case where the body surface temperature of the subject acquired by the temperature sensor is equal to or higher than a predetermined second temperature.

The notification unit can issue a warning in a case where the temporal change of the gel region is not detected by the gel region detection unit even though it is detected that the ultrasound probe and a hand of the examiner are positioned near the subject on the basis of the temperature distribution acquired by the temperature sensor.

In a case where the gel with a color different from a color of a body surface of the subject is applied to the examination position of the subject, the gel region detection unit can include a color sensor that acquires a color distribution in the body surface of the subject, and a temporal change detection unit that detects the temporal change of the gel region where the gel is applied to the subject by analyzing the color distribution acquired by the color sensor.

The ultrasound diagnostic apparatus can further include an ultrasound probe; an image acquisition unit that acquires an ultrasound image at the examination position of the subject by performing transmission and reception of an ultrasound beam using the ultrasound probe; and a monitor that displays the ultrasound image.

The ultrasound diagnostic apparatus can further include a body mark setting unit that displays a body mark on the monitor on the basis of the examination position of the subject estimated by the examination position estimation unit.

The body mark setting unit can select one of a pair of body marks representing the symmetrically disposed measurement sites of the subject on the basis of the examination position of the subject estimated by the examination position estimation unit, and display the selected body mark on the monitor.

The body mark setting unit can display a body mark in which a probe mark is drawn, on the monitor on the basis of the examination position of the subject estimated by the examination position estimation unit.

The ultrasound diagnostic apparatus can further include a checking unit that displays a dialog to check whether or not the body mark displayed on the monitor is correct, on the monitor.

A control method of an ultrasound diagnostic apparatus according to another aspect of the present invention is a control method of an ultrasound diagnostic apparatus for an examiner to perform ultrasonography on symmetrically disposed measurement sites of a subject by using an ultrasound probe, and the control method includes detecting a temporal change of a gel region where gel is applied to an examination position of the subject; and estimating the examination position of the subject on the basis of a position where the temporal change of the gel region is detected.

According to the present invention, the ultrasound diagnostic apparatus is an ultrasound diagnostic apparatus for an examiner to perform ultrasonography on symmetrically disposed measurement sites of a subject by using an ultrasound probe, and the ultrasound diagnostic apparatus includes a gel region detection unit that detects a temporal change of a gel region where gel is applied to an examination position of the subject; and an examination position estimation unit that estimates the examination position of the subject on the basis of a position where the temporal change of the gel region is detected by the gel region detection unit. Therefore, it is possible to accurately specify the examination position of the subject by the examiner while ensuring the subject's privacy.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
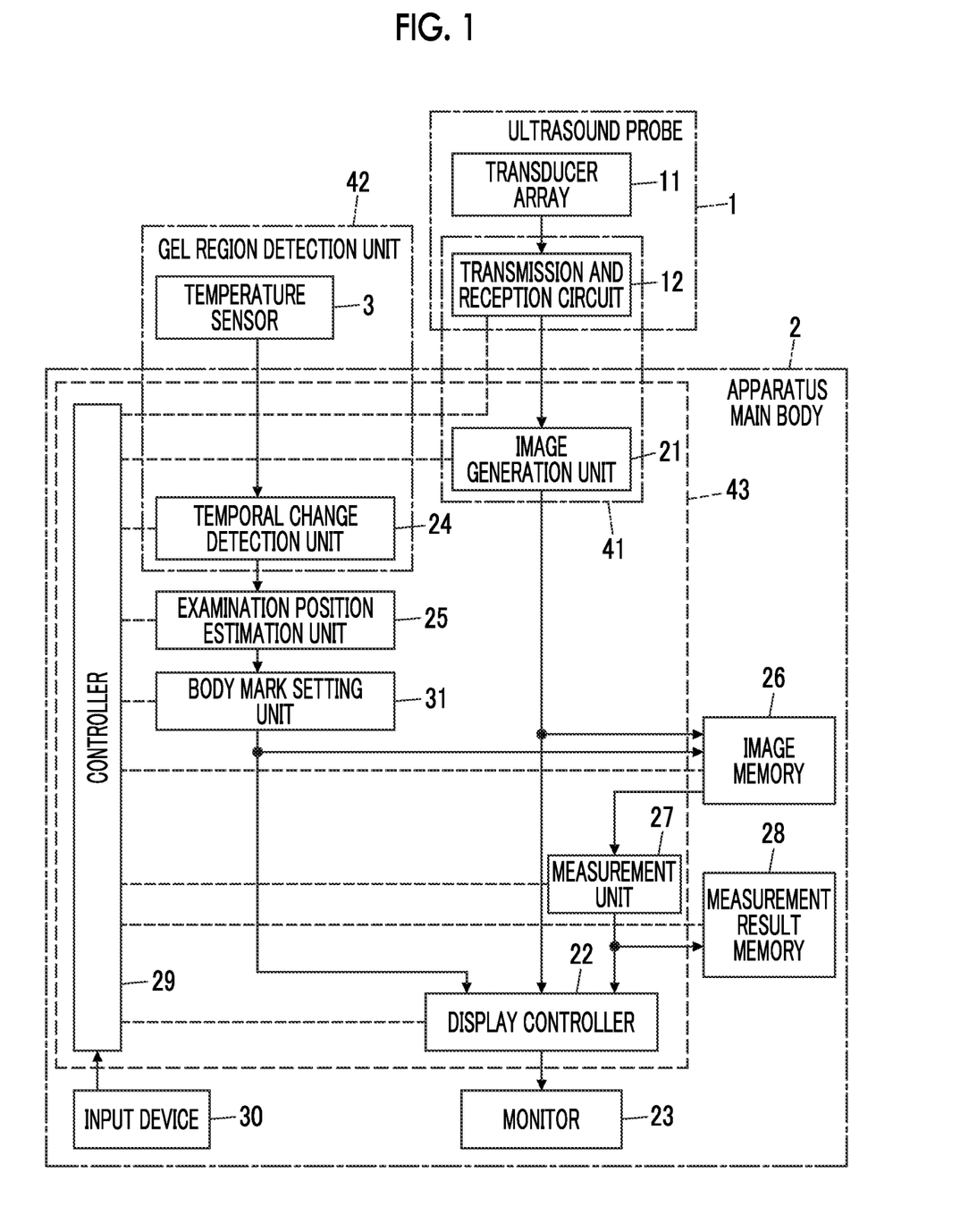
FIG. 1 is a block diagram illustrating a configuration of an ultrasound diagnostic apparatus according to a first embodiment of the present invention.

FIG. 1 illustrates a configuration of an ultrasound diagnostic apparatus according to a first embodiment of the present invention. The ultrasound diagnostic apparatus includes an ultrasound probe 1, an apparatus main body 2 connected to the ultrasound probe 1, and a temperature sensor 3 connected to the apparatus main body 2. The ultrasound diagnostic apparatus is used to perform ultrasonography on symmetrically disposed measurement sites of the subject such as the breast, kidneys, and lungs of the subject, for example.

The ultrasound probe 1 has a transducer array 11. A transmission and reception circuit 12 is connected to the transducer array 11.

The apparatus main body 2 has an image generation unit 21 connected to the transmission and reception circuit 12 of the ultrasound probe 1. Further, a display controller 22 and a monitor 23 are sequentially connected to the image generation unit 21. The apparatus main body 2 has a temporal change detection unit 24 connected to the temperature sensor 3. An examination position estimation unit 25 and a body mark setting unit 31 are sequentially connected to the temporal change detection unit 24. The display controller 22 is connected to the body mark setting unit 31. An image memory 26 is connected to the image generation unit 21 and the body mark setting unit 31. A measurement unit 27 is connected to the image memory 26. A measurement result memory 28 and the display controller 22 are connected to the measurement unit 27.

A controller 29 is connected to the transmission and reception circuit 12, the image generation unit 21, the display controller 22, the temporal change detection unit 24, the examination position estimation unit 25, the image memory 26, the measurement unit 27, the measurement result memory 28, and the body mark setting unit 31. An input device 30 is connected to the controller 29.

The image generation unit 21 of the ultrasound probe 1 and the transmission and reception circuit 12 of the apparatus main body 2 constitute an image acquisition unit 41. The temperature sensor 3 and the temporal change detection unit 24 of the apparatus main body 2 constitute a gel region detection unit 42. The image generation unit 21, the display controller 22, the temporal change detection unit 24, the examination position estimation unit 25, the measurement unit 27, the controller 29, and the body mark setting unit 31 of the apparatus main body 2 constitute a processor 43 for the apparatus main body 2.

The transducer array 11 of the ultrasound probe 1 has a plurality of ultrasonic transducers arranged in a one-dimensional or two-dimensional manner. According to a drive signal supplied from the transmission and reception circuit 12, each of the ultrasonic transducers transmits an ultrasonic wave and receives an ultrasound echo from the subject to output a signal based on the ultrasound echo. For example, each ultrasonic transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
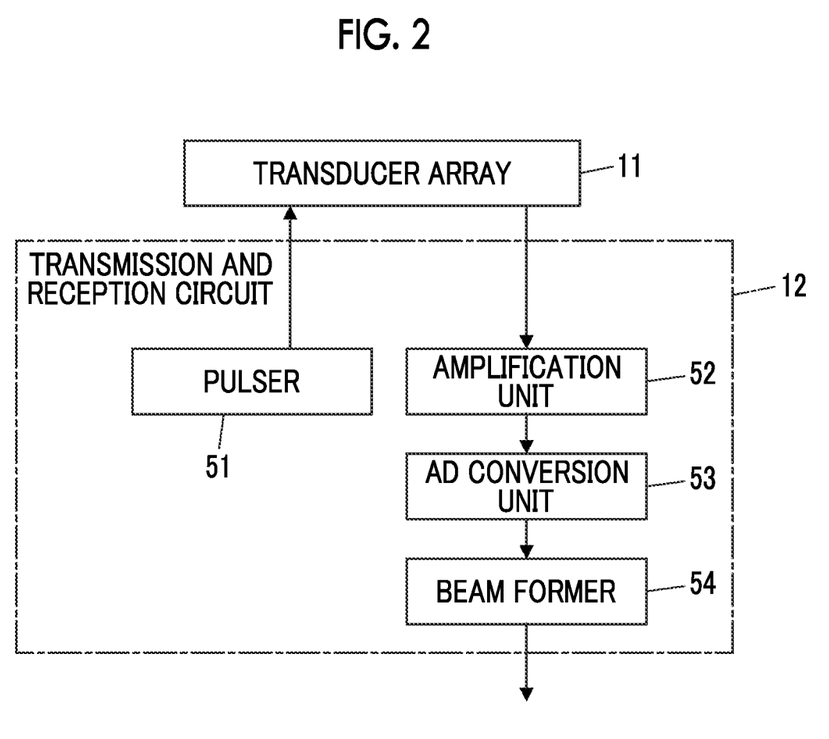
FIG. 2 is a block diagram illustrating a configuration of a transmission and reception circuit in the first embodiment of the present invention.

The transmission and reception circuit 12 causes the transducer array 11 to transmit the ultrasonic wave and generates a sound ray signal on the basis of a reception signal acquired by the transducer array 11, under the control of the controller 29. As illustrated in FIG. 2, the transmission and reception circuit 12 has a pulser 51 connected to the transducer array 11, and an amplification unit 52, an analog to digital (AD) conversion unit 53, and a beam former 54 that are sequentially connected in series from the transducer array 11.

The pulser 51 includes, for example, a plurality of pulse generators, and the pulser 51 adjusts the amount of delay of each drive signal so that ultrasonic waves transmitted from the plurality of ultrasonic transducers of the transducer array 11 form an ultrasound beam on the basis of a transmission delay pattern selected according to the control signal from the controller 29, and supplies the obtained signals to the plurality of ultrasonic transducers. Thus, in a case where a pulsed or continuous-wave voltage is applied to the electrodes of the ultrasonic transducers of the transducer array 11, the piezoelectric body expands and contracts to generate pulsed or continuous-wave ultrasonic waves from each ultrasonic transducer. From the combined wave of these ultrasonic waves, an ultrasound beam is formed.

The transmitted ultrasound beam is reflected by a target, for example, a site of the subject, and propagates toward the transducer array 11 of the ultrasound probe 1. The ultrasound echo propagating toward the transducer array 11 in this manner is received by each ultrasonic transducer constituting the transducer array 11. In this case, each ultrasonic transducer constituting the transducer array 11 expands and contracts by receiving the propagating ultrasound echo to generate a reception signal that is an electric signal, and outputs the reception signal to the amplification unit 52.

The amplification unit 52 amplifies the signals input from each ultrasonic transducer constituting the transducer array 11, and transmits the amplified signals to the AD conversion unit 53. The AD conversion unit 53 converts the signal transmitted from the amplification unit 52 into digital reception data. The beam former 54 performs so-called reception focusing processing in which addition is performed by giving delays to respective pieces of the reception data received from the AD conversion unit 53. Through the reception focusing processing, a sound ray signal in which each piece of the reception data converted by the AD conversion unit 53 is phased and added and the focus of the ultrasound echo is narrowed is acquired.

Figure 3:
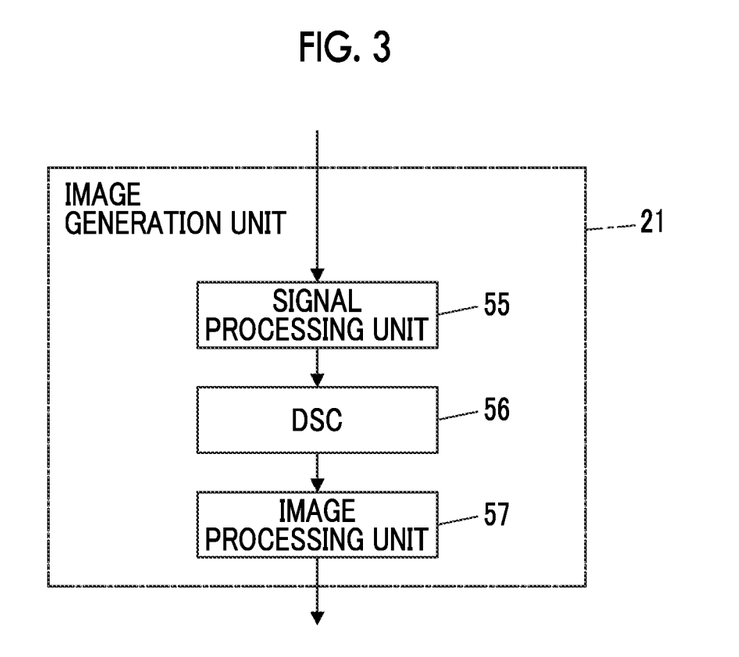
FIG. 3 is a block diagram illustrating a configuration of an image generation unit in the first embodiment of the present invention.

As illustrated in FIG. 3, the image generation unit 21 has a configuration in which a signal processing unit 55, a digital scan converter (DSC) 56, and an image processing unit 57 are sequentially connected in series.

The signal processing unit 55 generates a B-mode image signal, which is tomographic image information regarding tissues inside the subject, by performing, on the sound ray signal received from the transmission and reception circuit 12, correction of the attenuation due to the distance according to the depth of the reflection position of the ultrasonic wave using a sound speed value set by the controller 29 and then performing envelope detection processing.

The DSC 56 converts (raster conversion) the B-mode image signal generated by the signal processing unit 55 into an image signal according to a normal television signal scanning method.

The image processing unit 57 performs various kinds of necessary image processing such as gradation processing on the B-mode image signal input from the DSC 56, and then sends the B-mode image signal to the display controller 22 and the image memory 26. In the following, the B-mode image signal subjected to the image processing by the image processing unit 57 is simply referred to as an ultrasound image.

The display controller 22 performs predetermined processing on the ultrasound image or the like generated by the image generation unit 21, and displays the ultrasound image or the like on the monitor 23, under the control of the controller 29.

The monitor 23 performs various kinds of display under the control of the display controller 22. The monitor 23 can include a display device such as a liquid crystal display (LCD), or an organic electroluminescence (EL) display.

In general, in a case where the ultrasound image of the subject is captured by transmitting the ultrasonic waves from the ultrasound probe into the subject in a state where the ultrasound probe is in contact with the body surface of the subject, so-called gel is applied to the examination position on the body surface of the subject in some cases. The gel is also called ultrasound jelly, for example. By filling a gap between the body surface of the subject and the ultrasound probe with the gel, attenuation of ultrasonic waves between the body surface of the subject and the ultrasound probe can be suppressed, and a clear ultrasound image can be obtained. Here, the examination position refers to a position where the ultrasound probe is in contact with the body surface of the subject in the ultrasonography of the subject.

In a case where gel having a temperature different from the body surface temperature of the subject is applied to the examination position of the subject, the gel region detection unit 42 detects a temporal change of a gel region where the gel is applied to the examination position of the subject. In the following, the temperature sensor 3 and the temporal change detection unit 24 constituting the gel region detection unit 42 will be described.

The temperature sensor 3 is a sensor device that is configured by, for example, an infrared sensor and acquires a temperature distribution of the body surface of the subject. The temperature sensor 3 can acquire the temperature distribution of the body surface of the subject as a so-called thermal image, for example.

The temporal change detection unit 24 detects the gel region where the gel is applied and detects the temporal change of the gel region by analyzing the temperature distribution of the body surface of the subject acquired by the temperature sensor 3 from the past time point that goes back a predetermined time such as 1 second or a predetermined number of frames of thermal images, for example, 20 frames from the current time point, to the current time point.

The temporal change of the gel region refers to a change of the spatial distribution of the gel region in a certain time such as 1 second or 20 frames of the thermal images. The temporal change of the gel region includes a temporal change of the region where the gel is applied to the body surface of the subject before and after the application of the gel.

Here, in a case where the gel having a temperature higher than the body surface temperature of the subject is applied to the subject, the temperature of the region where the gel is to be applied is increased due to the application of the gel. Further, in a case where the gel having a temperature lower than the body surface temperature of the subject is applied to the subject, the temperature of the region where the gel is to be applied is decreased due to the application of the gel.

Thus, the temporal change detection unit 24 can store in advance a temperature threshold value (high temperature-side temperature threshold value) in a range of, for example, 39° C. to 40° C. that is higher than the body surface temperature of the general subject such as 35° C. to 37° C., and can detect a region having a temperature equal to or higher than the temperature threshold value as the gel region. Thus, the temporal change detection unit 24 can store in advance a temperature threshold value (low temperature-side temperature threshold value) in a range of, for example, 32° C. to 33° C. that is lower than the body surface temperature of the general subject such as 35° C. to 37° C., and can detect a region having a temperature equal to or lower than the temperature threshold value as the gel region.

In this manner, for example, the temporal change detection unit 24 can detect, as the gel region, a region with a certain temperature difference or more on the high temperature side or low temperature side with respect to the body surface temperature of the general subject such as 35° C. to 37° C.

For example, since the gel is applied to the body surface of the subject by bringing a distal end portion of the ultrasound probe 1 in a state where the gel is applied to the distal end portion of the ultrasound probe 1 into contact with the body surface of the subject, the spatial distribution of the gel region on the body surface of the subject is changed before and after the application of the gel to the subject. Further, in a case where the ultrasound probe 1 is moved on the body surface of the subject in a state where the gel is applied to the examination position of the subject and the ultrasound probe 1 is disposed on the gel, the gel is spread on the body surface of the subject so that the distribution of the spatial disposition of the gel region is changed. Therefore, the temporal change detection unit 24 can detect the temporal change of the distribution of the disposition of the gel region by detecting the change of the temperature on the body surface, for example, due to the application of the gel to the body surface of the subject on the basis of the temperature distribution of the body surface of the subject acquired by the temperature sensor 3. In a case of using the gel having a temperature higher than the body surface temperature of the subject, the temporal change detection unit 24 preferably has a configuration of detecting a temperature change from the body surface temperature of the subject to the high temperature side. Further, in a case of using the gel having a temperature lower than the body surface temperature of the subject, the temporal change detection unit 24 preferably has a configuration of detecting a temperature change from the body surface temperature of the subject to the low temperature side.

The temperature distribution of the ultrasound probe 1 and the temperature distribution of the examiner's hand holding the ultrasound probe 1 may be acquired overlapping the temperature distribution of the gel region depending on the position where the temperature sensor 3 is disposed. In this case, in order to accurately detect the temperature distribution of the gel region, the temporal change detection unit 24 can detect the temporal change of the gel region by excluding the temperature distributions of the ultrasound probe 1 and the examiner's hand from the temperature distribution acquired by the temperature sensor 3.

The examination position estimation unit 25 estimates the examination position of the subject by the examiner on the basis of the position where the temporal change of the gel region is detected by the temporal change detection unit 24.

In a case where the ultrasound probe 1 is moved on the body surface of the subject in a state where the gel is attached to the distal end portion of the ultrasound probe 1, the gel is spread on the body surface of the subject. Therefore, the examination position estimation unit 25 can determine that a location where the temporal change detection unit 24 has detected the temporal change of the distribution of the disposition of the gel region is a position immediately after the ultrasound probe 1 is moved on the body surface of the subject, and estimate the location as the examination position.

The body mark setting unit 31 stores a plurality of body marks in advance, determines the measurement site on the basis of the examination position of the subject estimated by the examination position estimation unit 25, and displays the body mark corresponding to the determined measurement site on the monitor 23. In this case, for example, in a case where the examination position estimated by the examination position estimation unit 25 is any position on the left breast of the subject, the body mark setting unit 31 can determine that the measurement site is the left breast of the subject.

Figure 4:
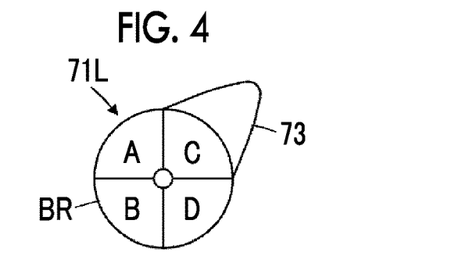
FIG. 4 is a diagram illustrating an example of a body mark representing a left breast in the first embodiment of the present invention.
Figure 5:
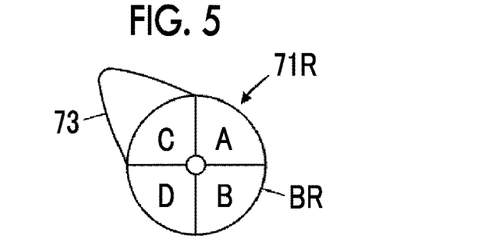
FIG. 5 is a diagram illustrating an example of a body mark representing a right breast in the first embodiment of the present invention.

Here, the body mark is a figure that imitates the site of the subject, and is generally used for indicating the examination position. As the body mark, for example, as illustrated in FIGS. 4 and 5, a body mark 71L indicating the left breast of the subject and a body mark 71R indicating the right breast of the subject are known.

The body mark 71L schematically indicates the left breast viewed from the front, and has a circular breast region BR and a substantially triangular axillary region 73 representing the armpit and extending obliquely upward from the breast region BR. The breast region BR is divided into four regions of an inner upper region A, an inner lower region B, an outer upper region C, and an outer lower region D of the breast, and the axillary region 73 is connected to a left oblique upper portion of the outer upper region C.

The body mark 71R schematically indicates the right breast viewed from the front, and is obtained by horizontally reversing the body mark 71L indicating the left breast.

The body mark setting unit 31 can select one of a pair of body marks representing the symmetrically disposed measurement sites of the subject such as the breast on the basis of the examination position of the subject estimated by the examination position estimation unit 25, and display the selected body mark on the monitor 23.

Further, the body mark setting unit 31 can also display on the monitor 23 the body mark in which a so-called probe mark indicating the examination position is drawn, on the basis of the examination position of the subject estimated by the examination position estimation unit 25. Although not illustrated, for example, in a case where the examination position estimation unit 25 estimates the location corresponding to the inner upper region A of the left breast as the examination position, the body mark 71L with the probe mark disposed on the inner upper region A of the body mark 71L imitating the left breast can be displayed on the monitor 23.

The image memory 26 stores the ultrasound image generated by the image generation unit 21 and the body mark set by the body mark setting unit 31 in association with each other, under the control of the controller 29.

Here, as the image memory 26, for example, recording media such as a flash memory, a hard disk drive (HDD), a solid state drive (SSD), a flexible disk (FD), a magneto-optical disk (MO disk), a magnetic tape (MT), a random access memory (RAM), a compact disc (CD), a digital versatile disc (DVD), a secure digital card (SD card), or a universal serial bus memory (USB memory) can be used.

The measurement unit 27 reads out the ultrasound image stored in the image memory 26, and performs the measurement of the subject for the examination position corresponding to the ultrasound image on the basis of the read-out ultrasound image, under the control of the controller 29. The measurement unit 27 can measure dimensions or the like of anatomical structures shown in the ultrasound image on the basis of the input operation by the examiner via the input device 30, for example.

The measurement result memory 28 stores the measurement result by the measurement unit 27 in association with the ultrasound image used for the measurement, under the control of the controller 29. As the measurement result memory 28, for example, recording media such as a flash memory, an HDD, an SSD, an FD, an MO disk, an MT, a RAM, a CD, a DVD, an SD card, or a USB memory can be used.

The input device 30 accepts the input operation by the examiner, and sends the input information to the controller 29. The input device 30 is configured by, for example, a device for the examiner to perform an input operation, such as a keyboard, a mouse, a trackball, a touchpad, a touch panel, or the like.

The processor 43 configured by the image generation unit 21, the display controller 22, the temporal change detection unit 24, the examination position estimation unit 25, the measurement unit 27, the controller 29, and the body mark setting unit 31 of the apparatus main body 2 is configured by a central processing unit (CPU) and a control program for causing the CPU to execute various kinds of processing, but the processor 43 may be configured by using a field programmable gate array (FPGA), a digital signal processor (DSP), an application specific integrated circuit (ASIC), a graphics processing unit (GPU), or another integrated circuit (IC) or may be configured by a combination thereof.

In addition, the image generation unit 21, the display controller 22, the temporal change detection unit 24, the examination position estimation unit 25, the measurement unit 27, the controller 29, and the body mark setting unit 31 of the processor 43 can also be configured by being integrated partially or entirely into one CPU or the like.

Next, an example of the operation of the ultrasound diagnostic apparatus according to the first embodiment will be described using the flowchart illustrated in FIG. 6. In the following description, it is assumed ultrasonography is performed on the symmetrically disposed measurement sites of the subject such as the breast, kidneys, and lungs of the subject.

First, in Step S1, the temperature sensor 3 continuously acquires the temperature distribution of the body surface of the subject, and the image acquisition unit 41 continuously acquires the ultrasound images that are tomograms at the examination position of the subject. In this case, while the temperature distribution of the body surface of the subject is acquired by the temperature sensor 3, the examiner applies the gel on the body surface of the subject and then disposes the distal end portion of the ultrasound probe 1 on the gel, or brings the distal end portion of the ultrasound probe 1 into contact with the body surface of the subject in a state where the gel is applied to the distal end portion of the ultrasound probe 1. Further, the reception signals are generated by the transducer array 11 of the ultrasound probe 1 transmitting the ultrasound beams into the subject and receiving the ultrasound echoes from the subject. The transmission and reception circuit 12 of the image acquisition unit 41 performs so-called reception focusing processing on the reception signals to generate sound ray signals, under the control of the controller 29. The sound ray signals generated by the transmission and reception circuit 12 are sent to the image generation unit 21. The image generation unit 21 generates the ultrasound image using the sound ray signals sent from the transmission and reception circuit 12.

The information on the temperature distribution of the body surface of the subject continuously acquired by the temperature sensor 3 is sent to the temporal change detection unit 24. The ultrasound images continuously acquired by the image acquisition unit 41 are sent to the display controller 22 and the image memory 26. The ultrasound images continuously sent to the display controller 22 are sequentially displayed on the monitor 23.

Next, in Step S2, the temporal change detection unit 24 detects the gel applied to the subject on the basis of the information on the temperature distribution of the body surface of the subject continuously acquired in Step S1, and detects the temporal change of the gel region on the subject. In this case, the temporal change detection unit 24 can analyze the continuously acquired temperature distribution of the body surface of the subject from the past time point that goes back a predetermined time such as 1 second or a predetermined number of frames of thermal images, for example, 20 frames from the current time point, that is, the latest time point at which the temperature distribution of the body surface of the subject is acquired in Step S1, to the latest time point, and detect a region having a temperature equal to or higher than the high temperature-side temperature threshold value stored in advance or a region having a temperature equal to or lower than the low temperature-side temperature threshold value stored in advance, as the gel region.

The temporal change detection unit 24 can detect the temporal change of the distribution of the disposition of the gel region for a predetermined time such as 1 second or 20 frames of the thermal images as the temporal change of the gel region.

In Step S3, the examination position estimation unit 25 estimates the examination position of the subject by the examiner on the basis of the position where the temporal change of the gel region is detected in Step S2. For example, the examination position estimation unit 25 can determine that the location where the temporal change detection unit 24 has detected the temporal change of the distribution of the disposition of the gel region in Step S2 is a position immediately after the ultrasound probe 1 is moved on the body surface of the subject, and estimate the location as the examination position.

In Step S4, the body mark setting unit 31 determines the measurement site on the basis of the examination position estimated in Step S3. For example, in a case where the estimated examination position is any position on the left breast of the subject, the body mark setting unit 31 can determine that the measurement site is the left breast of the subject.

In this manner, by the processing of Step S1 to Step S4, the measurement site is automatically determined on the basis of the temporal change of the gel region, and therefore, the measurement site can be accurately determined. Further, since the measurement site can be determined on the basis of the temperature distribution of the body surface of the subject, for example, without acquiring the optical image of the subject, it is possible to ensure the subject's privacy without acquiring the optical image in which the face of the subject is shown, for example.

In Step S5, the body mark setting unit 31 sets a body mark corresponding to the measurement site determined in Step S4. For example, in a case where it is determined in Step S4 that the measurement site is the left breast, the body mark 71L imitating the left breast illustrated in FIG. 4 is set.

In Step S6, the ultrasound images continuously acquired in Step S1 are sequentially displayed on the monitor 23, and the body mark set in Step S5 is displayed on the monitor 23 together with the sequentially displayed ultrasound images. In this case, the body mark set in Step S5 and the ultrasound image acquired in a state where the body mark is set are stored in the image memory 26 by being associated with each other.

The examiner can clearly understand the current examination position and the measurement site by checking the ultrasound image and the body mark displayed on the monitor 23, and therefore, can smoothly perform the ultrasonography. Since the body mark and the ultrasound image are automatically stored in the image memory 26 by being associated with each other, for example, it is not necessary for the examiner to perform processing of manually associating the body mark and the ultrasound image, and thus it is possible to smoothly perform the ultrasonography. After the ultrasonography, since the doctor can check the body mark accurately set corresponding to the measurement site and the ultrasound image in association with each other, the accuracy of the diagnosis can be improved.

In Step S7, the controller 29 determines whether to end the ultrasonography. The controller 29 can determine to end the ultrasonography in a case where an instruction to end the ultrasonography is input by the examiner via the input device 30, for example. Further, the controller 29 can determine to continue the ultrasonography in a case where an instruction to end the ultrasonography is not input by the examiner via the input device 30, for example.

In a case where it is determined to continue the ultrasonography in Step S7, the processing returns to Step S1, and the processing of Step S1 to Step S7 is performed again. In a case where it is determined to end the ultrasonography in Step S7, the operation of the ultrasound diagnostic apparatus according to the flowchart of FIG. 6 is ended.

As described above, with the ultrasound diagnostic apparatus according to the first embodiment, the temporal change of the gel region is detected by the temporal change detection unit 24 on the basis of the temperature distribution of the body surface of the subject acquired by the temperature sensor 3, and the examination position of the subject by the examiner is automatically estimated by the examination position estimation unit 25 on the basis of the detected temporal change of the gel region. Therefore, it is possible to accurately specify the examination position of the subject by the examiner while ensuring the subject's privacy.

In the ultrasound diagnostic apparatus of the first embodiment, since the examination position of the subject by the examiner is estimated on the basis of the temperature distribution of the body surface of the subject acquired by the temperature sensor 3, an expensive and complicated apparatus configuration such as an optical camera or a magnetic sensor for detecting the position of the ultrasound probe 1 is not required, and the examination position can be simply and accurately estimated in spite of an inexpensive and simple apparatus configuration.

The description has been made in which the image generation unit 21 is included in the apparatus main body 2, but the image generation unit 21 can be included in the ultrasound probe 1 instead of being included in the apparatus main body 2.

The disposed position of the temperature sensor 3 is not particularly limited as long as the examination position on the body surface of the subject and the temperature distribution of the gel region can be acquired at the position. For example, the temperature sensor 3 can be disposed near an examination table on which the subject lies during the ultrasonography, can be disposed on the ceiling of the room where the ultrasonography is performed, or can be mounted on the head or the like of the examiner.

In order to accurately detect the temporal change of the gel region even in a case where the subject is moving during the ultrasonography, the temporal change detection unit 24 can perform registration of the subject's body with the thermal image acquired by the temperature sensor 3 before detecting the temporal change of the gel region, for example. In this case, for example, the temporal change detection unit 24 can perform the registration using a known technique such as a registration method based on so-called template matching or so-called optical flow, or a registration method by detecting the body boundary of the subject.

Figure 6:
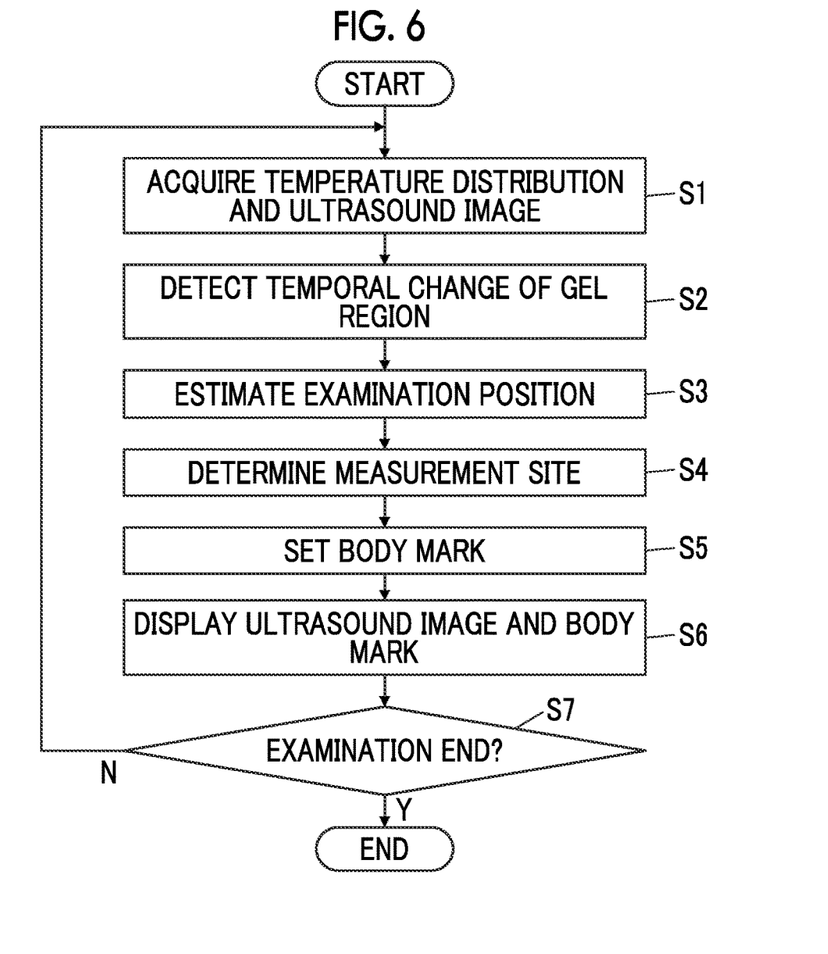
FIG. 6 is a flowchart illustrating an operation of the ultrasound diagnostic apparatus according to the first embodiment of the present invention.

In the flowchart of FIG. 6, measurement processing by the measurement unit 27 can be added. For example, after the ultrasound image and the body mark are displayed on the monitor 23 in Step S6 and are stored in the image memory 26, the measurement by the measurement unit 27 can be performed. In this case, the measurement unit 27 can read out the ultrasound image stored in Step S6 from the image memory 26, and measure the dimension or the like of the anatomical structure in the ultrasound image on the basis of the input operation by the examiner via the input device 30. The measurement result acquired by the measurement unit 27 in this manner is stored in the measurement result memory 28.

The description has been made in which the ultrasound image generated by the image generation unit 21 and the body mark set by the body mark setting unit 31 are automatically stored in the image memory 26, but for example, in a case where the examiner issues a so-called freezing instruction via the input device 30, the image memory 26 can store the body mark and the ultrasound image that is displayed in a freezing manner. Here, the freezing and the display in a freezing manner are to temporarily stop the display of the ultrasound images that are continuously displayed as a video on the monitor 23 and to display the ultrasound image of the latest one frame as a static image. As a result, only the ultrasound image desired by the examiner can be stored in the image memory 26.

In this case, the measurement unit 27 can perform measurement on the ultrasound image displayed in a freezing manner.

The description has been made in which the measurement site is determined while continuously acquiring the temperature distribution of the body surface of the subject and the ultrasound images in the flowchart of FIG. 6, but the measurement site can also be determined with the fact that the freezing instruction is issued by the examiner via the input device 30 as a trigger, for example. In this case, the processing for determining the measurement site is not always performed, but is performed only in a case where the freezing instruction is issued, and therefore, it is possible to reduce a computational load of the processor 43 during the ultrasonography.

As a result, even in a case where the processing power of the CPU constituting the processor 43 is low, processing required to be performed by the processor 43, for example, processing of generating and displaying the ultrasound image, processing of measuring the anatomical structure in the ultrasound image, and the like can be performed smoothly. The power consumption by the processor 43 can be reduced.

The information on the temperature distribution of the body surface of the subject acquired by the temperature sensor 3 can be stored in the image memory 26 in association with the ultrasound image generated by the image generation unit 21, for example. In a case where the temperature sensor 3 acquires the thermal image as the temperature distribution of the body surface of the subject and in a case where the thermal image of a facial portion of the subject is acquired, for example, the controller 29 can detect the facial portion of the subject in the thermal image, and exclude the image of the detected portion from the entire thermal image. In this case, the controller 29 can make the face of the subject indiscriminable by painting out the facial portion of the subject in the thermal image, for example. As a result, the subject's privacy can be ensured.

Although not illustrated, the ultrasound probe 1 can include a gel temperature management unit that keeps the temperature of the gel applied to the body surface of the subject at the distal end portion of the ultrasound probe 1 within a certain range. The gel temperature management unit includes, for example, a so-called heating wire or a Peltier element, and can keep the temperature of the gel within a certain range by heating or cooling the gel. As a result, for example, since the temperature of the gel region in contact with the distal end portion of the ultrasound probe 1 can be higher or lower than the body surface temperature of the subject, the temporal change detection unit 24 can more reliably detect the gel region in the vicinity of the distal end portion of the ultrasound probe 1, and the examination position estimation unit 25 can more accurately estimate the examination position.

Second Embodiment

Figure 7:
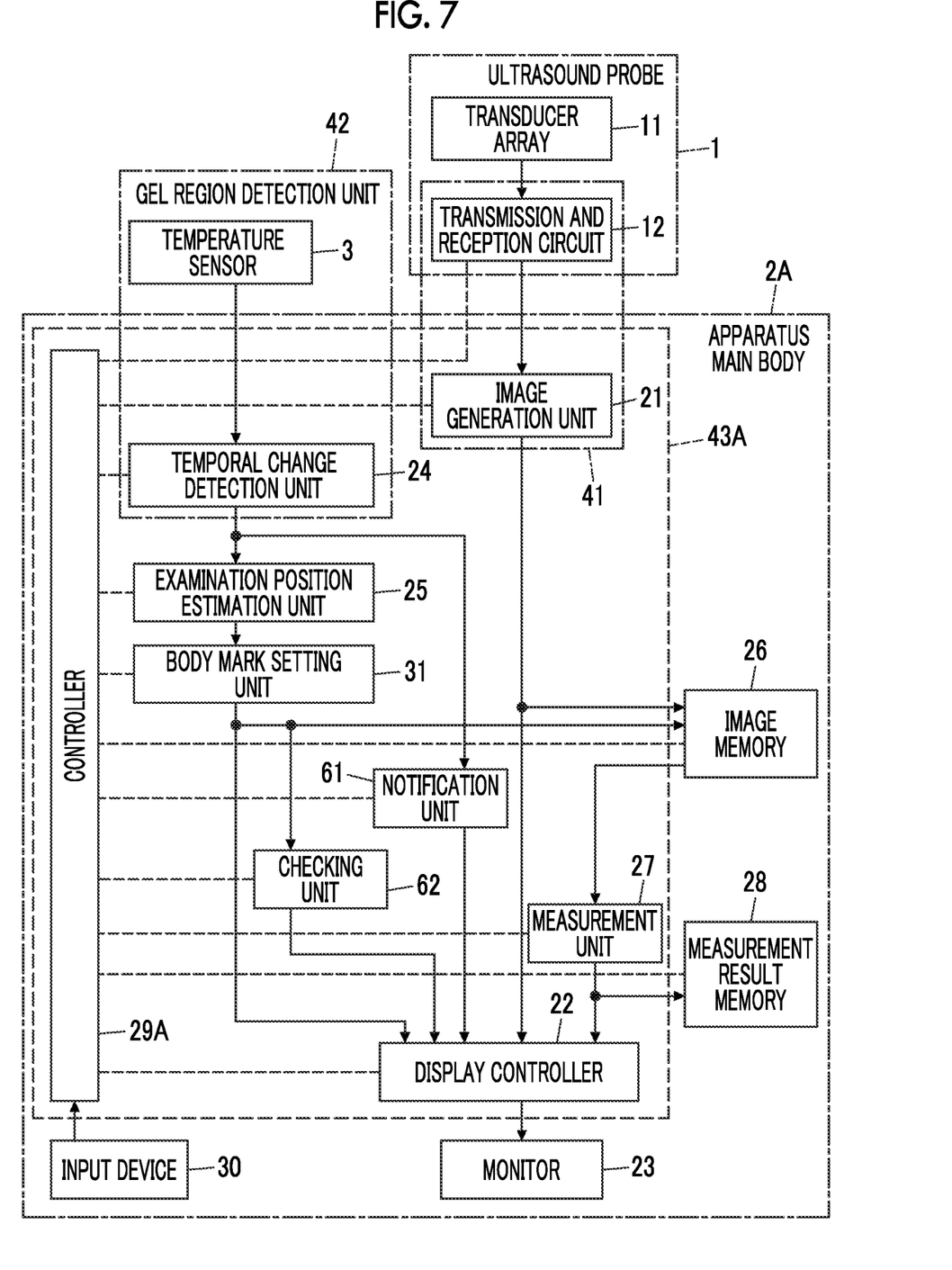
FIG. 7 is a block diagram illustrating a configuration of an ultrasound diagnostic apparatus according to a second embodiment of the present invention.

In a case where the ultrasonography is performed in a state where the gel is applied to the body surface of the subject, the temperature of the gel region approaches the body surface temperature of the subject over time, and thus the gel region may not be detected in the information on the temperature distribution acquired by the temperature sensor 3. In this case, the ultrasound diagnostic apparatus can issue a warning to the examiner.

FIG. 7 illustrates a configuration of an ultrasound diagnostic apparatus according to a second embodiment. The ultrasound diagnostic apparatus of the second embodiment is obtained by including an apparatus main body 2A instead of the apparatus main body 2 in the ultrasound diagnostic apparatus of the first embodiment illustrated in FIG. 1. The apparatus main body 2A is obtained by adding a notification unit 61 and a checking unit 62 and including a controller 29A instead of the controller 29 in the apparatus main body 2 in the first embodiment.

In the apparatus main body 2A, the notification unit 61 is connected to the temporal change detection unit 24. The notification unit 61 is connected to the display controller 22 and the controller 29A. The checking unit 62 is connected to the body mark setting unit 31. The display controller 22 and the controller 29A are connected to the checking unit 62. The image generation unit 21, the display controller 22, the temporal change detection unit 24, the examination position estimation unit 25, the measurement unit 27, the controller 29A, the body mark setting unit 31, the notification unit 61, and the checking unit 62 constitute a processor 43A for the apparatus main body 2A.

The notification unit 61 performs a notification to the examiner by displaying a message on the monitor 23, for example. Here, it is considered that the temperature of the gel gradually approaches the body surface temperature of the subject in a state where the gel is applied. Thus, for example, in a case where gel having a temperature higher than the body surface temperature of the subject is applied to the examination position of the subject and the temperature of the gel region acquired by the temperature sensor 3 is lowered to be equal to or lower than a predetermined first temperature, the notification unit 61 can issue a warning to the examiner. In some cases, it may be difficult for the temporal change detection unit 24 to detect the gel region in a case where the temperature of the gel region approaches the body surface temperature of the subject, but it is possible for the examiner to easily understand that the temperature of the gel region approaches the body surface temperature of the subject by checking the warning, and to apply the gel having a temperature higher than the body surface temperature of the subject to the examination position of the subject again.

In a case of applying the gel having a temperature higher than the body surface temperature of the subject to the examination position of the subject, in a case where the body surface temperature of the subject is high due to subject's fever or the like, it may be difficult for the temporal change detection unit 24 to detect the gel region. Thus, for example, the notification unit 61 can issue a warning in a case where the body surface temperature of the subject acquired by the temperature sensor 3 is equal to or higher than a predetermined second temperature. As a result, it is possible for the examiner to easily understand that the gel region cannot be detected because the body surface temperature of the subject is high. In this case, it is possible for the examiner to take a measure such as applying the gel having a temperature lower than the body surface of the subject to the body surface of the subject, for example.

Thus, for example, in a case where gel having a temperature lower than the body surface temperature of the subject is applied to the examination position of the subject and the temperature of the gel region acquired by the temperature sensor 3 is increased to be equal to or higher than a predetermined third temperature, the notification unit 61 can issue a warning to the examiner. It is possible for the examiner to easily understand that the temperature of the gel region approaches the body surface temperature of the subject by checking the warning, and to apply the gel having a temperature lower than the body surface temperature of the subject to the examination position of the subject again.

In a case where the temporal change of the gel region is not detected by the temporal change detection unit 24 even though it is detected that the ultrasound probe 1 and the examiner's hand are positioned near the subject on the basis of the temperature distribution of the body surface of the subject acquired by the temperature sensor 3, the notification unit 61 can issue a warning to the examiner. It is possible for the examiner to easily understand that the temperature of the gel region approaches the body surface temperature of the subject by checking the warning, and to apply the gel having a temperature higher than the body surface temperature of the subject or the gel having a temperature lower than the body surface temperature of the subject to the examination position again.

In a case where the temporal change detection unit 24 cannot detect the gel region due to the approach of the temperature of the gel region to the body surface temperature of the subject, the examination position estimation unit 25 cannot accurately estimate the examination position, and therefore, it is difficult for the body mark setting unit 31 to correctly set the body mark corresponding to the current examination position. Thus, the checking unit 62 displays on the monitor 23 a dialog to check whether or not the body mark displayed on the monitor 23 is correct, that is, whether or not the body mark is a body mark corresponding to the actual examination position. Even in a case where an incorrect body mark is set, the examiner can set a correct body mark again by checking the dialog.

As described above, with the ultrasound diagnostic apparatus according to the second embodiment, in a case where the temperature of the gel region where the gel having a temperature higher than the body surface temperature of the subject is applied is lowered to be equal to or lower than the predetermined first temperature, in a case where the temperature of the gel region where the gel having a temperature lower than the body surface temperature of the subject is applied is increased to be equal to or higher than the predetermined third temperature, in a case where the body surface temperature of the subject is equal to or higher than the predetermined second temperature, or in a case where the temporal change of the gel region is not detected even though it is detected that the ultrasound probe 1 and the examiner's hand are positioned near the subject, a warning can be issued by the notification unit 61, and therefore, the examiner can take a measure such as applying the gel to the examination position again such that the temporal change of the gel region is normally detected. Further, since a dialog to check whether or not the body mark displayed on the monitor 23 is correct is displayed on the monitor 23 by the checking unit 62, even in a case where an incorrect body mark is set, the examiner can set a correct body mark again.

The checking unit 62 can determine whether or not the examination position estimated by the examination position estimation unit 25 is in the vicinity of a center line dividing the left and right sides of the subject in a case where the subject is viewed from the front, and can display a dialog on the monitor 23 only in a case where the examination position is determined to be in the vicinity of the center line. In this case, for example, the checking unit 62 can have a predetermined distance threshold value for the shortest distance between the examination position and the center line, and can determine that the examination position is in the vicinity of the center line in a case where the shortest distance between the examination position and the center line is equal to or less than the distance threshold value. In this manner, in a case where the examination position is positioned in the vicinity of the center line of the subject, the examiner can set an accurate body mark more reliably by checking the dialog.

Third Embodiment

Figure 8:
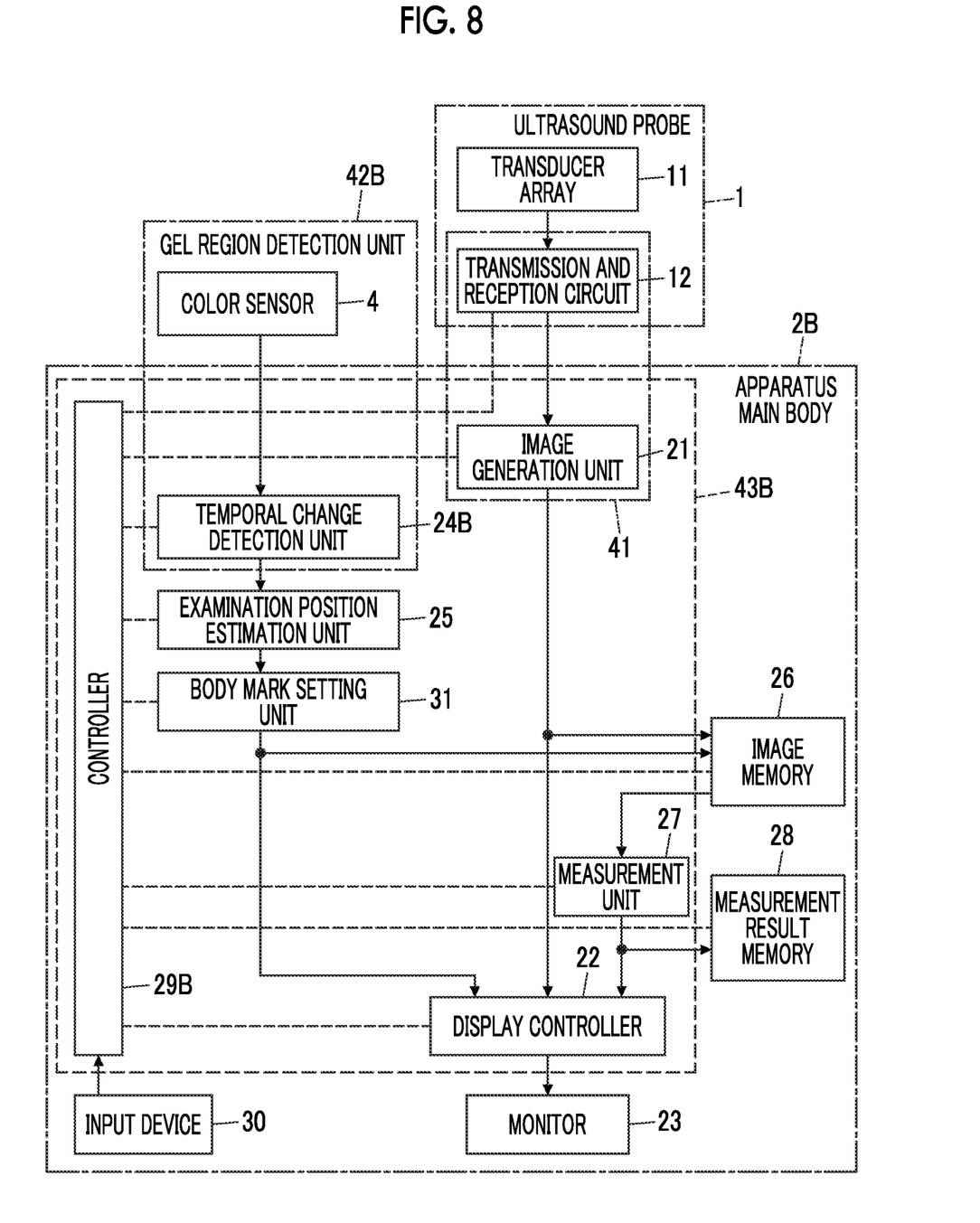
FIG. 8 is a block diagram illustrating a configuration of an ultrasound diagnostic apparatus according to a third embodiment of the present invention.

The description has been made in which the temporal change of the gel region is detected on the basis of the temperature distribution of the body surface of the subject, but the temporal change of the gel region can be detected even by acquiring a specific color in the body surface of the subject, for example.

FIG. 8 illustrates a configuration of an ultrasound diagnostic apparatus according to a third embodiment. The ultrasound diagnostic apparatus of the third embodiment is obtained by including an apparatus main body 2B instead of the apparatus main body 2 and including a color sensor 4 instead of the temperature sensor 3 in the ultrasound diagnostic apparatus of the first embodiment illustrated in FIG. 1. The apparatus main body 2B is obtained by including a temporal change detection unit 24B instead of the temporal change detection unit 24 and including a controller 29B instead of the controller 29 in the apparatus main body 2 in the first embodiment.

In the apparatus main body 2B, the temporal change detection unit 24B is connected to the color sensor 4. Further, the color sensor 4 and the temporal change detection unit 24B constitute a gel region detection unit 42B. The image generation unit 21, the display controller 22, the temporal change detection unit 24B, the examination position estimation unit 25, the measurement unit 27, the controller 29B, and the body mark setting unit 31 constitute a processor 43B for the apparatus main body 2B.

The color sensor 4 is a sensor device that acquires a color distribution in the body surface of the subject. For example, the color sensor 4 can include a so-called optical sensor or the like that detects a specific color such as red, blue, and green, and can acquire a color distribution in the body surface by detecting reflected light from the body surface of the subject.

In a case where the gel with a color different from the color of the body surface of the subject is applied to the examination position of the subject, the temporal change detection unit 24B analyzes the color distribution of the body surface of the subject acquired by the color sensor 4 to detect the gel region on the body surface and to detect the temporal change of the detected gel region.

The temporal change detection unit 24B detects a region with a color different from the color of the body surface of the subject as the gel region by referring to the color distribution acquired by the color sensor 4 from the past time point that goes back a certain time such as 1 second or a predetermined number of frames of thermal images, for example, 20 frames from the current time point, to the current time point, for example. Further, the temporal change detection unit 24B can detect the temporal change of the distribution of the disposition of the gel region on the basis of the color distribution of the body surface of the subject acquired by the color sensor 4.

In this manner, for example, since it is not required to use an optical camera or the like for detecting the temporal change of the gel region, it is possible to ensure the subject's privacy without acquiring an optical image in which the subject's face is shown, for example.

The examination position estimation unit 25 estimates the examination position of the subject by the examiner on the basis of the temporal change of the gel region detected by the temporal change detection unit 24B.

The body mark setting unit 31 determines the measurement site on the basis of the examination position of the subject estimated by the examination position estimation unit 25, and automatically sets the body mark corresponding to the determined measurement site.

As described above, in a case where the examination position of the subject is estimated on the basis of the color distribution of the body surface of the subject acquired by the color sensor 4, the temporal change of the gel region is detected by the temporal change detection unit 24B on the basis of the color distribution of the body surface of the subject acquired by the color sensor 4, and the examination position of the subject by the examiner is automatically estimated by the examination position estimation unit 25 on the basis of the detected temporal change of the gel region. Therefore, as in the case where the examination position of the subject is estimated on the basis of the temperature distribution of the body surface of the subject acquired by the temperature sensor 3, it is possible to accurately specify the examination position of the subject by the examiner while ensuring the subject's privacy.

Further, it has been described that the content of the third embodiment is applied to the first embodiment, but the content of the third embodiment can be similarly applied to the second embodiment. That is, instead of the temperature sensor 3, the color sensor 4 can be provided in the ultrasound diagnostic apparatus of the second embodiment illustrated in FIG. 7.

EXPLANATION OF REFERENCES

1: ultrasound probe
2, 2A, 2B: apparatus main body
3: temperature sensor
4: color sensor
11: transducer array
12: transmission and reception circuit
21: image generation unit
22: display controller
23: monitor
24, 24B: temporal change detection unit
25: examination position estimation unit
26: image memory
27: measurement unit
28: measurement result memory
29, 29A, 29B: controller
30: input device
31: body mark setting unit
41: image acquisition unit
42, 42B: gel region detection unit
43, 43A, 43B: processor
51: pulser
52: amplification unit
53: AD conversion unit
54: beam former
55: signal processing unit
56: DSC
57: image processing unit
61: notification unit
62: checking unit
71L, 71R: body mark
73: axillary region
A: inner upper region
B: inner lower region
C: outer upper region
D: outer lower region

What is claimed is:

1. An ultrasound diagnostic apparatus for an examiner to perform ultrasonography on measurement sites of a subject by using an ultrasound probe, the ultrasound diagnostic apparatus comprising:
the ultrasound probe;
a temperature sensing device configured to sequentially acquire a temperature distribution of a body surface of the subject;
a monitor; and
a processor configured to:
detect a temporal change of a gel region where gel is applied to an examination position of the subject by sequentially analyzing the temperature distribution sequentially acquired by the temperature sensing device, where a gel having a temperature different from a body surface temperature of the subject is applied to the examination position in the gel region;
estimate a position where the temporal change of the gel region is detected as the examination position;
acquire an ultrasound image at the examination position of the subject by performing transmission and reception of an ultrasound beam using the ultrasound probe; and
display the ultrasound image on the monitor.

2. The ultrasound diagnostic apparatus according to claim 1,
wherein the measurement sites are any one of breasts, kidneys, or lungs.

3. The ultrasound diagnostic apparatus according to claim 1,
wherein the processor is further configured to detect the temporal change of the gel region by excluding the ultrasound probe and a hand of the examiner from the temperature distribution acquired by the temperature sensing device.

4. The ultrasound diagnostic apparatus according to claim 3,
wherein the processor is further configured to perform a notification to the examiner.

5. The ultrasound diagnostic apparatus according to claim 1,
wherein the processor is further configured to perform a notification to the examiner.

6. The ultrasound diagnostic apparatus according to claim 5,
wherein the gel having a temperature higher than the body surface temperature of the subject is applied to the examination position of the subject, and
the processor is further configured to issue a warning in a case where a temperature of the gel region acquired by the temperature sensing device is lowered to be equal to or lower than a predetermined first temperature.

7. The ultrasound diagnostic apparatus according to claim 6,
wherein the processor is further configured to issue a warning in a case where the body surface temperature of the subject acquired by the temperature sensing device is equal to or higher than a predetermined second temperature.

8. The ultrasound diagnostic apparatus according to claim 6,
wherein processor is further configured to issue a warning in a case where the temporal change of the gel region is not detected even though it is detected that the ultrasound probe and a hand of the examiner are positioned near the subject based on the temperature distribution acquired by the temperature sensing device.

9. The ultrasound diagnostic apparatus according to claim 5,
wherein the processor is further configured to issue a warning in a case where the body surface temperature of the subject acquired by the temperature sensing device is equal to or higher than a predetermined second temperature.

10. The ultrasound diagnostic apparatus according to claim 5,
wherein processor is further configured to issue a warning in a case where the temporal change of the gel region is not detected even though it is detected that the ultrasound probe and a hand of the examiner are positioned near the subject based on the temperature distribution acquired by the temperature sensing device.

11. The ultrasound diagnostic apparatus according to claim 1,
wherein the processor is further configured to display a body mark on the monitor based on the examination position of the subject which is estimated.

12. The ultrasound diagnostic apparatus according to claim 11,
wherein the processor is further configured to:
select one of a pair of body marks representing the measurement sites of the subject based on the examination position of the subject which is estimated, and display the selected body mark on the monitor.

13. The ultrasound diagnostic apparatus according to claim 12,
wherein the processor is further configured to display a body mark in which a probe mark is drawn, on the monitor based on the examination position of the subject which is estimated.

14. The ultrasound diagnostic apparatus according to claim 12, further comprising:
wherein the processor is further configured to display a dialog to check whether or not the body mark displayed on the monitor is correct, on the monitor.

15. A control method of an ultrasound diagnostic apparatus for an examiner to perform ultrasonography on measurement sites of a subject by using an ultrasound probe, the ultrasound diagnostic apparatus including the ultrasound probe and a monitor, the control method comprising:
sequentially acquiring a temperature distribution of a body surface of the subject;
detecting a temporal change of a gel region where gel is applied to an examination position of the subject by sequentially analyzing the acquired temperature distribution, where a gel having a temperature different from a body surface temperature of the subject is applied to the examination position in the gel region;
estimating a position where the temporal change of the gel region is detected as the examination position;
acquiring an ultrasound image at the examination position of the subject by performing transmission and reception of an ultrasound beam using the ultrasound probe; and
displaying the ultrasound image on the monitor.

* * * * *